United States Patent [19]

Crowell et al.

[11] Patent Number: 5,932,432
[45] Date of Patent: Aug. 3, 1999

[54] EXPRESSION LIBRARY SCREEN BY PRENYLATION OF EXPRESSED PROTEINS

[75] Inventors: Dring N. Crowell, Indianapolis; Brenda Biermann, Zionsville; Stephen Randall, Speedway, all of Ind.

[73] Assignee: Indiana University Foundation, Bloomington, Ind.

[21] Appl. No.: 08/785,795

[22] Filed: Jan. 21, 1997

Related U.S. Application Data

[63] Continuation of application No. 08/283,875, Aug. 1, 1994, abandoned.

[51] Int. Cl.$^6$ .............................. C12Q 1/48; C12Q 1/68; G01N 33/58
[52] U.S. Cl. ........................... 435/15; 435/7.1; 435/7.72; 435/6
[58] Field of Search ............................... 435/6, 7.1, 7.72, 435/15

[56] References Cited

PUBLICATIONS

Anant, J.S., Ong. O.C., Xie, H., Clarke, S., O'Brien, P.J. and Fung, B.K.–K., "In Vivo Differential Prenylation of Retinal Cyclic GMP Phosphodiesterase Catalytic Subunits", *J. Biol. Chem.,* vol. 267, pp. 687–690 (1992).
Battey, N.H. and Venis, M.A., "Calcium–Dependent Protein Kinase From Apple Fruit Membranes Is Calmodulin–Independent But Has Calmodulin–Like Properties", *Planta,* vol. 176, pp. 91–97 (1988).
Bednarek, S.Y., Reynolds, T.L., Schroeder, M., Grabowski, R., Hengst, L., Gallwitz, D. and Raikhel, N.V., "A Small GTP–Binding Protein From *Arabidopsis Thaliana* Functionally Complements The Yeas YPT6 Null Mutant", *Plant Physiol.,* vol. 104, pp. 591–596 (1994).
Bowler, C., Neuhaus, G., Yamagata, H. and Chua, N.–H., "Cyclic GMP And Calcium Mediate Phytochrome Phototransduction", *Cell,* vol. 77, pp. 73–81 (1994).
Clarke, S., "Protein Isoprenylation And Methylation At Carboxyl–Terminal Cysteine Residues", *Annu. Rev. Biochem.,* vol. 61, pp. 355–386 (1992).
Celenza, J.L. and Carlson, M., "A Yeast Gene That Is Essential For Release From Glucose Repression Encodes A Protein Kinase", *Science,* pp. 1175–1180 (Sep. 12, 1980).
Crowell, D.N. and Amasino, R.M., "Induction Of Specific mRNAs In Cultures Soybean Cells During Cytokinin Or Auxin Starvation", *Plant Physiol.,* vol. 95, pp. 711–715 (1991).
Davis, T.N., Urdea, M.S., Masiarz, F.R. and Thorner, J., "Isolation Of The Yeast Calmodulin Gene: Calmodulin Is An Essential Protein", *Cell,* vol. 47, pp. 423–431 (1986).
Frederick, S.E., Mangan, M.E., Carey, J.B. and Gruber, P.J., "Intermediate Filament Antigens Of 60 And 65 kDa In The Nuclear Matrix Of Plants: Their Detection And Localization", *Exp. Cell Res.,* vol. 199, pp. 213–222 (1992).
Fukada, Y., Takao, T., Ohguro, H., Yoshizawa, T., Akino, T. and Shimonishi, Y., "Farnesylated Gamma–Subunit Of Photoreceptor G Protein Indispensable For GTP–Binding", *Nature,* vol. 346, pp. 658–660 (1990).

Fukui, Y. and Kaziro, Y., "Molecular Cloning And Sequence Analysis Of A Ras Gene From Schizosaccharomyces Pombe", *EMBO J.,* vol. 4, No. 3, pp. 687–691 (1985).
Hancock, J.F., Magee, A.I., Childs, J.E. and Marshall, C.J., "All Ras Proteins Are Polyisoprenylated But Only Some Are Palmitoylated", *Cell,* vol. 57, pp. 1167–1177 (1989).
Inglese, J., Glickman, J.F., Lorenz, W., Caron, M.G. and Lefkowitz, R.J., "Isoprenylation Of A Protein Kinase", *J. Biol. Chem.,* vol. 267, pp. 1422–1425 (1992).
Inglese, J., Kock, W.J., Caron, M.G. and Lefkowitz, R.J., "Isoprenylation In Regulation Of Signal Transduction By G–Protein–Coupled Receptor Kinases", *Nature,* vol. 359, pp. 147–150, (1992).
Jackson, J.H., Cochrane, C.G., Bourne, J.R., Solski, P.A., Buss, J.E. and Der, C.J., "Farnesol Modification Of Kirsten––Ras Exon 4B Protein Is Essential For Transformation", *Proc. Natl. Acad. Sci., U. S. A.,* vol. 87, pp. 3042–3046 (1990).
James, G.L., Goldstein, J.L., Pathak, R.K., Anderson, R.G.W. and Brown, M.S., "PxF, A Prenylated Protein Of Peroxisomes", *J. Biol. Chem.,* vol. 269, pp. 14182–14190 (1994).
Kearns, E.V. and Assmann, S.M., "The Guard Cell–Environment Connection", *Plant Physiol.,* vol. 102, pp. 711–715 (1993).
Kennelly, P.J. and Krebs, E.G., "Consensus Sequences As Substrate Specificity Determinants For Protein Kinases And Protein Phosphatases", *J. Biol. Chem.,* vol. 266, No. 24, pp. 15555–15558 (1991).
Kieber, J.J., Rothenberg, M., Roman, G., Feldmann, K.A. and Ecker, J.R., "CTR1, A Negative Regulator Of The Ethylene Response Pathway In Arabidopsis, Encodes a Member Of The Raf Family Of Protein Kinases", *Cell,* vol. 72, pp. 427–444 (1993).

(List continued on next page.)

*Primary Examiner*—Jasemine C. Chambers
*Assistant Examiner*—Scott D. Priebe
*Attorney, Agent, or Firm*—Woodard, Emhardt, Naughton, Moriarty & McNett

[57] ABSTRACT

Described is a novel in vitro method for obtaining and identifying proteins which, in their natural in vivo setting, are covalently modified after translation. To identify novel isoprenylated proteins for subsequent biochemical study, colony blots of a Glycine max cDNA expression library were [$^3$H] farnesyl labeled in vitro. Proteins identified by this screen contained several different carboxy-termini that conform to consensus farnesylation motifs. These proteins included known farnesylated proteins (DnaJ homologs) and several novel proteins, two of which contained 6 or more tandem repeats of a hexapeptide having the consensus sequence [E or G] [G or P]EK[P or K]K. Expression library screening by direct labeling can thus be adapted to recover and identify isoprenylated proteins as well as proteins with other post-translational modifications. This identification and recovery further enables the recovery of transformants containing DNA encoding the proteins, as well as the raising of antibodies to the proteins.

9 Claims, 3 Drawing Sheets

PUBLICATIONS

Kinsella, B.T and Maltese, W.A., "Rab GTP–Binding Proteins With Three Different Carboxyl–Terminal Cysteine Motifs Are Modified In Vivo By 20–Carbon Isoprenoids", *J. Biol. Chem.,* vol. 267, No. 6, pp. 3940–3945 (1992).

Maltese, W.A. and Robishaw, J.D., "Isoprenylation Of C–Terminal Cystein In A G–Protein Gamma Subunit", *J. Biol. Chem.,* vol. 265, pp. 18071–18074 (1990).

Maru, Y. and Witte, O.N., "The BCR Gene Encodes A Novel Serine/Threonine Kinase Activity Within A Single Exon", *Cell,* vol. 67, pp. 459–468 (1991).

McGrath, J.P., Capon, D.J., Smith, D.H., Chen, E.Y., Seeburg, P.H., Goeddel, D.V. and Levinson, A.D., "Structure And Organzation Of The Human Ki–Ras Proto–Oncogene And A Related Processed Pseudogene", *Nature,* vol. 304, pp. 501–506 (1983).

McNulty, A.K. and Saunders, M.J., "Purification And Immunological Detection Of Pea Nuclear Intermediate Filaments: Evidence For Plant Nuclear Lamins", *J. Cell Sci.,* vol. 103, pp. 407–414 (1992).

Moores, S.L., Schaber, M.D., Mosser, S.D., Rands, E., O'Hara, M.B., Garsky, V.M., Marshall, M.S., Pompliano, D.L. and Gibbs, J.B., "Sequence Dependence Of Protein Isoprenylation", *J. Biol. Chem.,* vol. 266, pp. 14603–14610 (1991).

Mumby, S.M., Casey, P.C., Gil , A.G., Gutowski, S. and Sternweis, P.C., "G Protein Gamma Subunits Contain A 20–Carbon Isoprenoid", *Proc. Natl. Acad. Sci., U.S.A.,* vol. 87, pp. 5873–5877 (1990).

Pearson, W.R. and Lipman, D.J., "Improved Tools For Biological Sequence Comparison", *Proc. Natl. Acad. Sci., U.S.A.,* vol. 85, pp. 2444–2448 (1988).

Randall, S.K., Marshall, M.S. and Crowell, D.N., "Protein Isoprenylation In Suspension–Cultured Tobacco Cells", *Plant Cell,* vol. 5, pp. 433–442 (1993).

Sambrook, J., Fritsch, E.F. and Maniatis, T., *Molecular Cloning: A Laboratory Manual* (Cold Spring Harbor Laboratory, Cold Spring Harbor, NY).

Schafer, W.R., Kim, R., Sterne, R., Thorner, J., Kim, S.–H. and Rine, J., "Genetic And Pharmacological Suppression Of Oncogenic Mutations In Ras Genes Of Yeast And Humans", *Science,* vol. 245, pp. 379–384 (1989).

Shimizu, K., Birnbaum, D., Ruley, M.A., Fasano, O., Suard, Y., Edlund, L., Taparowsky, E., Goldfarb, M. and Wigler, M., "Structure of The Ki–Ras Gene Of the Human Lung Carcinoma Cell Line Calu–1", *Nature,* vol. 304, pp. 497–500 (1983).

Stein, R.B., Robinson, P.S. and Scolnick, E.M., "Photoaffinity Labeling With GTP Of Viral P21 Ras Protein Expressed In *Escherichia Coli",* J. Virol., vol. 50, pp. 343–351 (1984).

Temeles, G.L., Gibbs, J.B., D'Alonzo, J.S., Sigal, I.S. and Scolnick, E.M., "Yeast And Mammalian Ras Proteins Have Conserved Biochemical Properties", *Nature,* vol. 313, pp. 700–703 (1985).

Terryn, N., Van Montagu, M. and Inze, D., "GTP–Binding Proteins In Plants", *Plant Mol. Biol.,* vol. 22, pp. 143–152 (1993).

Tong, C.–G., Dauwalder, M., Clawson, G.A., Hatem. C.L. and Roux, S.J., "The Major Nucleoside Triphjosphatase In Pea (*Pisum Sativum* L.) Nuclei And In Rat Liver Nuclei Share Common Epitopes Also Present In Nuclear Lamins", *Plant Physiol.,* vol. 101, pp. 1005–1011 (1993).

Vorbueger, K., Kitten, G.T. and Nigg, E.A., "Modification Of Nuclear Lamin Proteins By A Mevalonic Acid Derivative Occurs In Reticulocyte Lysates And Requires The Cysteine Residue Of The C–Terminal CXXM Motif", *EMBO J.,* vol. 8, pp. 4007–4013 (1989).

Wildman, D.E., Tamir, H., Leberer, E., Northup, J.K. and Dennis, M., "Prenyl Modification Of Guanine Nucleotide Regulatory Protein Gamma$_2$ Subunits Is Not Required For Interaction With The Transducin Alpha Subunit Or Rhodopsin", *Proc. Natl. Acad. Sci., U.S.A.,* vol. 90, pp. 794–798 (1993).

Wolda, S.L. and Glomset, J.A.., "Evidence For Modification Of Lamin B By A Product Of Mevalonic Acid", *J. Biol. Chem.,* vol. 263, pp. 5997–6000 (1988).

Yang, Z. and Watson, J.C., "Molecular Cloning And Characterization Of Rho, A Ras–Related Small GTP–Binding Protein From The Garden Pea", *Proc. Natl. Acad. Sci., U.S.A.,* vol. 90, pp. 8732–8736 (1993).

Zhu, J.–K., Bressan, R.A. and Hasegawa, P.M., "Isoprenylation Of The Plant Molecular Chaperone ANJ1 Facilitates Membrane Association And Function At High Temperature", *Proc. Natl. Acad. Sci., U.S.A.,* vol. 90, pp. 8557–8561 (1993).

Zhu, J.–K., Shi, J., Bressan, R.A. and Hasegawa, P.M., "Expression Of An *Atriplex Nummularia* Gene Encoding A Protein Homologous To The Bacterial Molecular Chaperone DnaJ", *Plant Cell,* vol. 5, pp. 341–349 (1993).

Biermann et al., Plant Physiology 105 (Suppl. 1) pp. 32 (May 24, 1994).

Carmel et al., Analytical Biochemistry 203:274–280 (1992).

Singh et al. Cell 52:415–423 (1988).

Gershoni et al Analytical Biochemistry 131:1–15 (1983).

A

```
GMFP1  LYIQFNVDFP DSGFLSPDQC QLLEKVLPQK SSKHVSDMEL DDCEETTLHD  50
         || ||||||| ||   |||  ||   ||||   |||  |||  | |||||||
ANJ1   MYIHFTVEFP DS..LNPDQV KSLEAILPPK PSMSLTYMEL DECEETTLHN  399

GMFP1  VNFKEEMRRK QQQQYREAYD EDDDEPSGQR VQCAQQ               86
       || |||||||  | || |||| |||  | |||  |||||
ANJ1   VNIEEEMKRK QTQAQQEAYD EDDEPAGGQR VQCAQQ               435
```

B

```
GMFP2               KAEKPKTE PEKKKDGGGE KPKEEPEKKK DGGEKPK...   35
                    || || || |||| ||||| ||| ||||||  ||||||
GMFP3  KPKAEPEKKK DGGGEKPKAE PEKKKDGGGE KPKAEPEKKK DGGEKPKGDA   50

GMFP2  .........P GPEKPKDKPT PAPLPVQPHI AAPMAVPVGM LYAPPPCYGG   76
                 | ||||||||   |||||||| |  ||||||| |||||||| |
GMFP3  PKKEAEKPKP GPEKPKDKPA PAPLPVQPHM AAPMAVPVGM LYAPPPCYEG   100

GMFP2  RPVGPGYEYG GPMLCYDGYY ARPVYDSYSG GRPCYGNRCD QYFSEENPQG   126
       ||||||||||  || ||| || |||||||| | |||| |  | ||| |||||||
GMFP3  RPVGPGYEYG GPMFCYDGYY ARPVYDSYGG GRPCYVNRGD QYFSEENPQG   150

GMFP2  CTIM  130
       | ||
GMFP3  CIIM  154
```

C

```
GMFP6  KLRKFCHVEI LSVGPAKEEP KKEEKKPEAK KDPKEEYAEL LKVVEANYYQ   50

GMFP6  TRHLQYPYYY SRTVEENPTG CVIC                              74
```

Fig. 3

EXPRESSION LIBRARY SCREEN BY PRENYLATION OF EXPRESSED PROTEINS

This application is a continuation of application Ser. No. 08/283,875, filed Aug. 1, 1994, now abandoned.

This invention was made with government support under the National Science Foundation grant number MCB-9220099, entitled "Protein Prenylation in Plants." The government has certain rights in the invention.

BACKGROUND OF THE INVENTION

The present invention generally relates to an in vitro method for identifying proteins which, in vivo, are covalently post-translationally modified, and for obtaining tranformants encoding such proteins. More particularly, the invention relates to a novel expression library screen for recovering and identifying isoprenylated proteins.

By way of further background, isoprenylated proteins are involved in eukaryotic cell growth and signal transduction. The protein determinant for prenylation is a short carboxy-terminal motif containing a cysteine, to which the isoprenoid is covalently attached via thioether linkage. To date, isoprenylated proteins have almost all been identified by demonstrating the attachment of an isoprenoid to previously known proteins. Thus, many isoprenylated proteins likely remain undiscovered.

Specific prenyl:protein transferases catalyze the transfer of farnesyl (FTase) or geranylgeranyl (GGTase) moieties from isoprenyl pyrophosphates to proteins. The protein determinant for prenylation is a short carboxy-terminal motif containing a cysteine, to which the isoprenoid is covalently attached via thioether linkage. For farnesylation, this motif is CaaX, where 'C' is cysteine, 'a' is usually an aliphatic amino acid, and 'X' is methionine, glutamine, serine, cysteine, or alanine (1). The type I GGTase recognizes a similar CaaX motif with a C-terminal leucine, whereas GGTase II prenylates proteins ending in XXCC, CCXX, or CXC (1). Many signal-transducing fungal and animal proteins are prenylated, including Ras (2–4), Ras-like small GTP-binding proteins (4), receptor kinases (5, 6), heterotrimeric G-protein gamma subunits (7–10) and retinal cGMP phosphodiesterase subunits (11). The biological significance of protein isoprenylation is underscored by the fact that unfarnesylated K-Ra protein is localized to the cytoplasm rather than the plasma membrane, and is incapable of cellular transformation (3, 4). Plants employ signalling pathways similar to those involving prenylated proteins in other organisms (12–14), but analogous prenylated proteins have not been characterized in plants. Nuclear lamins, which form the nuclear lamina and associate with chromatin and the nuclear envelope, are also prenylated in animals (15, 16). Lamin-like proteins have recently been discovered in plant nuclei, but it is not clear if these proteins are prenylated or associated with the nuclear envelope (17–19).

In tobacco suspension cultures, multiple proteins are prenylated in vivo, although their identities are not known (20). One plant protein is known to be prenylated in vivo: a farnesylated Atriplex protein designated ANJ1 that is homologous to the bacterial molecular chaperone DnaJ (21, 22). However, several plant cDNA-encoded small GTP-binding proteins have been shown to contain consensus geranylgeranylation sequences at the carboxy-terminus (23–25), indicating probable prenylation in vivo. Identification of isoprenylated proteins would provide a basis for future work on the role of protein isoprenylation in cellular processes.

A hamster isoprenylated protein was recently identified by purification from [$^3$H]-mevalonate-labelled cells (26). This approach cannot be readily applied to most eukaryotic tissues, due to insufficient mevalonate incorporation (20).

In light of this background, there persists a need for a method which can be used to readily obtain and identify isoprenylated proteins, both currently known and yet unknown. There also persists a need for methods for identifying transformant microorganisms containing genes encoding such proteins, and for raising antibodies to such proteins. The present invention addresses these needs.

SUMMARY OF THE INVENTION

Accordingly, one preferred embodiment of the invention provides a method for identifying a transformant containing DNA encoding a prenylated protein. The method includes the steps (i) establishing a pattern of distinct colonies of microorganisms from an expression library on a first substrate, the expression library including microorganisms containing introduced eukaryotic DNA; (ii) replicating said pattern of distinct colonies on at least a second substrate; (iii) causing protein synthesis by said distinct colonies on said second substrate and creating a protein blot therefrom containing distinct areas of protein corresponding to the distinct colonies; (iv) subjecting the protein blot to prenylation conditions with a labeled prenylation agent to identify one or more protein areas which contain prenylated protein; and (v) correlating said one or more protein areas containing prenylated protein to said first substrate to identify one or more transformant microorganisms containing DNA encoding a prenylated protein.

Broader aspects of the invention provide a method for identifying a transformant containing DNA encoding a subject protein, the subject protein being modifiable by a ligand which covalently or non-covalently specifically binds to the protein. The method comprises (i) establishing a pattern of distinct colonies of microorganisms from an expression library on a first substrate, the expression library including microorganisms containing introduced eukaryotic DNA; (ii) replicating said pattern of distinct colonies on at least a second substrate; (iii) causing protein synthesis by said distinct colonies on said second substrate and creating a protein blot therefrom containing distinct areas of protein corresponding to the distinct colonies; (iv) subjecting the protein blot to labeling conditions with said ligand containing a label in order to identify one or more protein areas which contain the subject protein; and (v) correlating said one or more protein areas containing said subject protein to said first substrate to identify one or more transformant microorganisms containing DNA encoding the subject protein.

Still another preferred embodiment of the invention provides a method for obtaining a protein blot useful in the identification of a transformant containing DNA encoding a subject protein, the subject protein being modifiable by a ligand which specifically binds to the protein. The method includes providing a protein blot comprising a replicate substrate having expressed protein from a pattern of distinct colonies of microorganisms containing introduced eukaryotic DNA, the pattern of distinct colonies being a replica of a pattern of distinct colonies on an original substrate. The protein blot is subjected to labeling conditions with the ligand which contains a label in order to identify one or more protein areas which contain the subject protein, so that the one or more protein areas are correlatable to the original substrate to identify onre or more colonies containing transformants expressing the subject protein.

The methods of the present invention provide ready access to prenylated proteins and to transformant microorganisms, such as bacteria, containing DNA encoding the same. Further, in accordance with the invention, the accessed prenylated proteins can be utilized, employing well-known and conventional techniques, to raise antibodies to the prenylated proteins. Such protocols commonly include introducing the protein into an animal of interest, e.g. a mammal, and recovering from the mammal antibodies which are thus raised to the protein, for example in the form of blood, blood serum, or purified fractions thereof containing the antibody. As indicated, such protocols are well known and will be readily applied by those skilled in the area in accordance with the invention. In addition, the invention is useful in assisting in determining the modes of action of substances such as pharmaceuticals, herbicides or insecticides, which provide ligands which specifically bind proteins. Screens of the invention can be employed to readily identify proteins interacting with such ligands and thus assist in mode of action studies.

Additional embodiments, features and advantages of the invention will be apparent from the descriptions herein.

DESCRIPTION OF THE FIGURES

FIG. 3 shows deduced peptide sequences of soybean cDNAs encoding farnesylated proteins. Sequences shown are peptides fused in frame to the vector-derived coding sequences, and termination codons are located 100–300 bases upstream of a poly (A) tail. Carboxy-terminal sequences conforming to the CaaX farnesylation motif are shown in bold type. Identical amino acids at a given position are indicated by dashes. Dots represent gaps introduced to optimize the alignment. (A) Alignment of the deduced amino acid sequence of GMFP1 (Seq. I.D. No.1) with ANJ1 (Seq. I.D. No.2), a farnesylated Atriplex protein homologous to E. coli DnaJ (21,22). (B) Comparison of novel soybean farnesylated proteins GMFP2 (Seq. I.D. No.3) and GMFP3 (Seq. I.D. No.4). Repeats of a peptide hexamer with the consensus sequence [E or G] [G or P]EK[P or K]K are underlined. (C) cDNA-encoded peptide GMFP6 (Seq. I.D. No.5). The region containing repeat motifs is underlined.

DESCRIPTION OF THE PREFERRED EMBODIMENT

Figure 1:
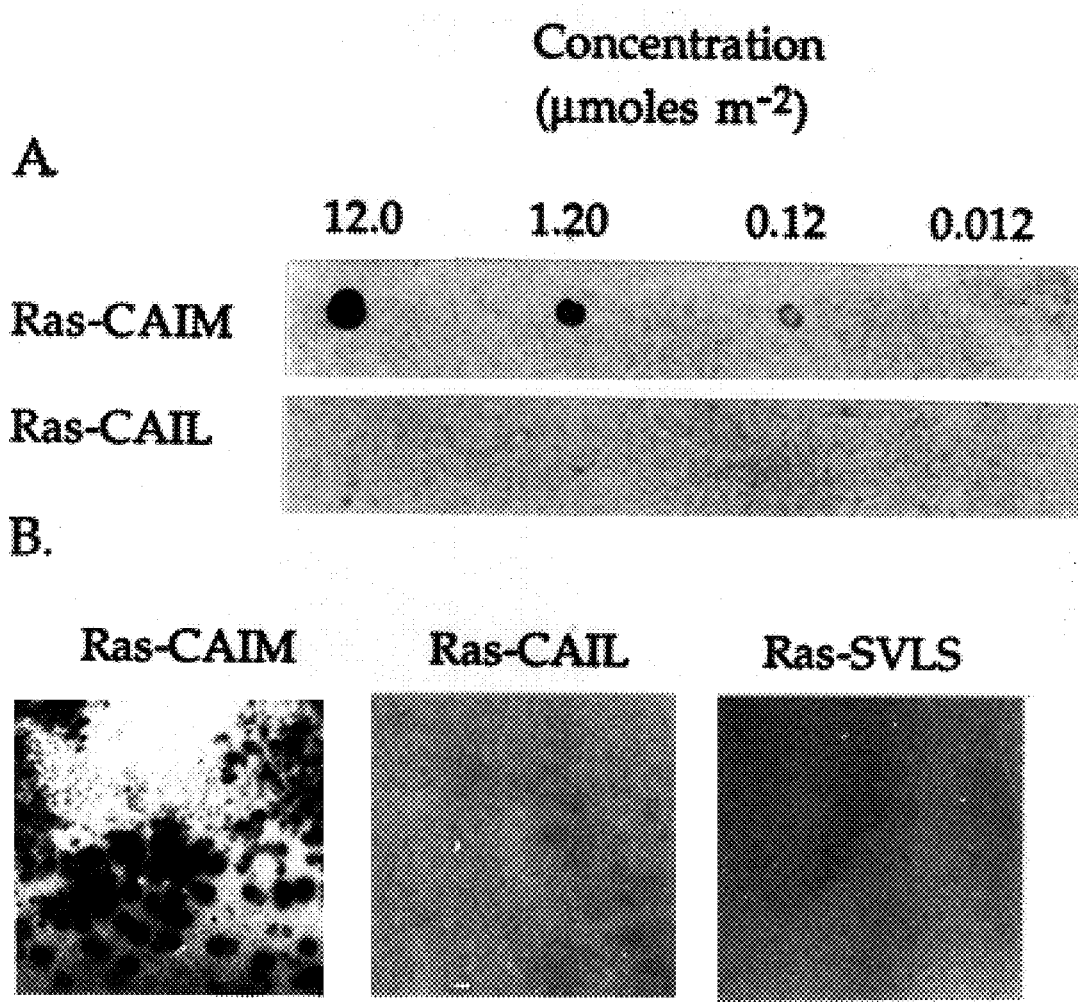
FIG. 1 shows that an FTase substrate can be specifically labeled and detected at concentrations greater than 0.12 mmol m$^{-2}$, and can be detected in bacterial colony blots. (A) Blots of purified proteins. Plasmid-encoded Ras proteins which are (Ras-CAIM) or are not (Ras-CAIL) FTase substrates (1) were purified from E. coli, and dotted on nylon filters. Filters were blocked, prenylated by incubating with [$^3$H] FPP and a tobacco extract containing FTase activity, washed with ethanol to remove unincorporated radioactivity, and fluorographed for 30 days. (B) Blots of bacterial colony lysates. Protein blots were made by alkaline lysis of E. coli colonies grown on nylon filters. Blots made from cells expressing Ras with the carboxy-terminal tetrapeptide CAIM, CAIL or SVLS (1) were treated as in (A).

For the purpose of promoting an understanding of the principles of the invention, reference will now be made to certain preferred embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

The following abbreviations are used herein: FPP, farnesyl pyrophosphate; FTase, farnesyl: protein transferase; GGTase, geranylgeranyl: protein transferase Ras Proteins The Ras proteins used in this study were encoded by pRAS1 plasmids containing a truncated yeast ras1 gene (1, 27,28). In pRAS1, the yeast ras1 gene is fused in the correct translational reading frame to the first 6 codons of lacZ, 5 polylinker codons, 9 codons from p21v-ras sequences upstream of and adjacent to the normal p21v-ras initiation codon and the first four codons of p21v-ras (27, 28). The 3' end of the yeast ras1 gene was subsequently truncated and altered by site-directed mutagenesis to encode the carboxy-terminal peptide CAIM, CAIL, or SVLS (1). (Permission to use these plasmids was obtained from Merck, Sharpe and Dohme Research Laboratories, West Point, Pa.) Yeast Ras1 was highly expressed as soluble protein (approx 10–20% of total protein) in E. coli strain RR1 lacI$^q$ (1, 28). Yeast Ras proteins with different carboxy-termini were expressed at similar levels. Expressed proteins were purified from E. coli cell extracts to greater than 90% purity by medium pressure liquid chromatography on a DEAE-Sepharose column (Pharmacia), and were eluted at approx 0.1 M in a 0–1.0 M NaCl gradient. Purified proteins were dot-blotted on Nytran plus (Schleicher and Schuell) membrane filters at different concentrations in Tris Buffered Saline (TBS, 50 mM Tris, pH 8.0, 150 mM NaCl) containing 1 mg/ml bovine serum albumin (BSA), and farnesyl labeled as described below.

Colony Protein Blots

Between 1×10$^3$ and 3×10$^4$ E. coli strain RR1 lacI$^q$ transformants (electroporation method, Bio-Rad Gene Pulser protocol) were spread on a 82 mm diameter nitrocellulose filter, which was overlaid on an LB plate containing 150 mg/l ampicillin (Amp) and incubated overnight at 37° C. A single replica was made onto a dry Nytran plus filter (29), and fusion protein synthesis was induced by placing the replica on an LB plate containing 150 mg/l Amp and 1 mM isopropyl-b-D-thiogalactopyranoside (IPTG) for 6 hours at 37° C. Original filters were then incubated for 6 hours on fresh LB plates containing 150 mg/l Amp, placed on Whatman #1 filter papers soaked in 10% glycerol, stored at −80° C., and later used to recover positive clones. Protein blots of lysed bacterial colonies were made by incubating replica filters sequentially on blotting paper soaked in the following solutions: A) 150 mM NaCl, 100 mM Tris, pH 8.0, 5 mM MgCl$_2$, 2 mg/ml DNase I, 50 mg/ml lysozyme, 20 min B) 150 mM NaCl, 100 mM NaOH, 0.1% SDS, 5 min C) 150 mM NaCl, 100 mM Tris HCl, pH 6.5, 5 min. Filters were then air dried and stored up to 1 week at 25° C. before blocking and prenyl labeling.

Farnesyl Labeling of Blots

Air dried filters were blocked by gently shaking in TBS containing 20 mg/ml BSA and 0.05% Tween 20 for 1–2 hours at 25° C. The blocking solution was changed 2–3 times. The filters were then rinsed, the bound proteins labeled with [$^3$H] farnesol by incubation in the presence of [$^3$H] FPP and the FTase present in a tobacco protein extract, and unincorporated label was washed away. The rinsing, labeling, and washing were done by vigorous rotary shaking at 30° C. in the following series of solutions: 1) TBS, 10 ml per 82 mm dia filter, 4×5 min; (2) Prenylation Buffer: 50 mM Hepes pH 7.5, 20 mM MgCl$_2$, 5 mM dithiothreitol, 5 ml/filter, 5 min; (3) Protein extract of a 2-day-old tobacco suspension culture (ref. 20) with Prenylation Buffer added fresh from a 4.4× concentrate, 1 ml/filter, 5 min; (4) Labeling solution as in #3 containing 4 mCi/ml [$^3$H] FPP (15 Ci/mmol, American Radiochemical), 1 ml/filter, 1 hour; (5) 1 ml/filter solution #3 added to labeling solution, 1 hour; (6) TBS, 10 ml/filter, 6×5 min; (7) 50% ethanol, 10 ml/filter, 3×5 min; (8) 100% ethanol, 10 ml/filter, 3×5 min. Filters were then air dried, dipped in Amplify (Amersham) fluorographic reagent, placed on plastic film backing, dried 1 hour at 50° C., and fluorographed 7–30 days at −80° C. with pre-flashed Kodak XAR5 film.

cDNA Library

The vector (pHEP1) was constructed by inserting the 141 bp Hind III/Pvu II fragment of pUC 19 into Hind III/Nde I-cut pRAS1, generating multiple cloning sites downstream of the ORF to which the yeast ras1gene had been fused (27). Soybean cell culture cDNA (30), amplified once in pBluescript SK II+ (Stratagene), was excised with Hind III (5') and Sac I (3') and ligated into the plasmid pHEP1.

SDS-PAGE of Farnesylated E. coli Proteins

Cultures were grown 12–15 hours at 37° C. in LB containing 150 mg/l Ampicillin and 1 mM IPTG and proteins were extracted (31). 2.5 ml of E. coli protein extract was farnesyl-labeled in a 12.5 ml volume by proteins extracted from either soybean or tobacco cell suspension cultures (20). SDS polyacrylamide gels (14%) of electrophoretically separated, labeled proteins were soaked in Amplify (Amersham), dried and fluorographed with Kodak XAR5 film 7–30 days at −80° C. The molecular mass of the fusion protein does not necessarily correspond to that of the corresponding plant protein, since the cDNA coding region may not all be present. Furthermore, vector-encoded amino acids comprise 3 kDa of the fusion protein molecular mass.

DNA Sequencing

Dideoxy nucleotide sequencing of both strands of cDNAs was according to Sequenase (U. S. Biochemical) protocols. Oligomers were synthesized to prime cDNA sequences distal to vector priming sites. Database searches were conducted with the FASTA and TFASTA programs (32).

RESULTS AND DISCUSSION

As a first step toward identifying soybean isoprenylated proteins, the sensitivity and specificity of in vitro prenylation of blotted proteins were tested. Plasmid-encoded yeast RAS1 proteins with the carboxy-terminal sequences CAIM, CAIL, or SVLS were prepared from E. coli clones obtained from Mark Marshall (1). Yeast and tobacco prenyltransferases show similar specificity toward these carboxy-termini: Ras-CAIM is preferentially farnesylated, Ras-CAIL is readily geranylgeranylated but not farnesylated, and Ras-SVLS is not a substrate for prenylation (1, 20). As shown in FIG. 1A, the lowest protein concentration detected by radiolabeling protein blots with [$^3$H] FPP in the presence of a tobacco extract was 0.12 mmol m$^{-2}$ for purified Ras-CAIM and $\leq$12 mmol m$^{-2}$ for Ras-CAIL.

LacZ fusion proteins expressed in E. coli bacteriophage 1 vectors are synthesized at up to 100 pg/plaque (0.001 mmol m$^{-2}$ for a protein of 100,000 Da) (29). This is about two orders of magnitude less than the minimum FTase substrate concentration detectable in our assays (FIG. 1A). Since expression levels are generally higher in plasmid libraries, we tested the feasibility of detecting prenylated proteins in such a library using colony blots of the plasmid-encoded Ras proteins described above. As shown in FIG. 1B, blotted proteins of E. coli colonies expressing Ras-CAIM were labeled by in vitro prenylation, demonstrating that bacterially-expressed FTase substrates could be detected by this method. Colony blots of bacteria expressing proteins which are not FTase substrates (Ras-CAIL and Ras-SVLS) had very weak or undetectable signals after prolonged autoradiography. These signals were readily distinguishable from the Ras-CAIM positive control (FIG. 1B). Thus, labeling of E. coli protein blots in the presence of [$^3$H] FPP was specific for colonies expressing a FTase substrate, indicating that the protein blotting and prenylation methods might be used to specifically identify farnesylated proteins among those encoded by a cDNA library. Since high levels of soluble recombinant protein were obtained from the vector expressing yeast Ras (1, 27, 28), we constructed a cDNA expression library in this vector by inserting soybean cDNAs into the restriction site ras1 had occupied. Approximately 3×10$^5$ cDNA-containing clones were screened by prenylating replica colony protein blots (29) with [$^3$H] FPP in the presence of a tobacco extract, resulting in the identification of 158 putative positive clones (see FIG. 2A). Cells on areas of filters where positive signals were obtained were re-screened. Of the colonies that produced a signal in the first screen, 72% were positive in the second screen. Molecular masses of prenylated proteins from positive colonies were determined (FIG. 2B) by prenylating E. coli culture extracts with [$^3$H] FPP in the presence of a tobacco or soybean cell culture extract, and separating the proteins by SDS-PAGE.

One soybean cDNA (Glycine max farnesylated protein 1, or GMFP1, FIG. 3A) encoded an 86 amino acid prenylated protein highly homologous (63% amino acid identity) to the carboxy-terminus of the Atriplex stress-induced protein ANJ1, the only plant protein known to be prenylated in vivo (21, 22). A similar clone (not shown) with approximately 95% peptide identity to GMFP1 and designated GMFP9, encoded an approximately 300 amino acid peptide homologous to ANJ1. ANJ1 is structurally related to E. coli DnaJ, and is thought to function as a molecular chaperone (22).

Two cDNAs encoding similar proteins, GMFP2 and GMFP3, (FIG. 3B) predominated among the cDNAs encoding farnesylated proteins. Sequence analyses and DNA hybridizations (29) of positive clones revealed that more than 90% of the cDNA clones selected by protein farnesyl-labeling were structurally similar to GMFP2 and GMFP3. DNA and deduced peptide sequences of GMFP2 and GMFP3 were not similar to other sequences in the GenBank database. Both deduced peptide sequences had basic regions containing 6 or 8 repeats of a hexapeptide having the consensus sequence [E or G] [G or P]EK[P or K]K. Most of these repeats were separated by 1 or 2 amino acids (FIG. 3B). Cysteine residues 110 and 115 of GMFP2 and 134 of GMFP3 are possible sites for palmitoylation. GMFP6 (FIG. 3C) has structural features similar to GMFP2 and GMFP3: the C-terminal peptide EENPXGCXIX is conserved (SEQ ID NO:4–6), as well as a repeat motif rich in glutamate, lysine and proline. Several different farnesylated proteins identified from Arabidopsis and tobacco expression libraries have these same two structural features suggesting that they are functionally related.

Figure 2:
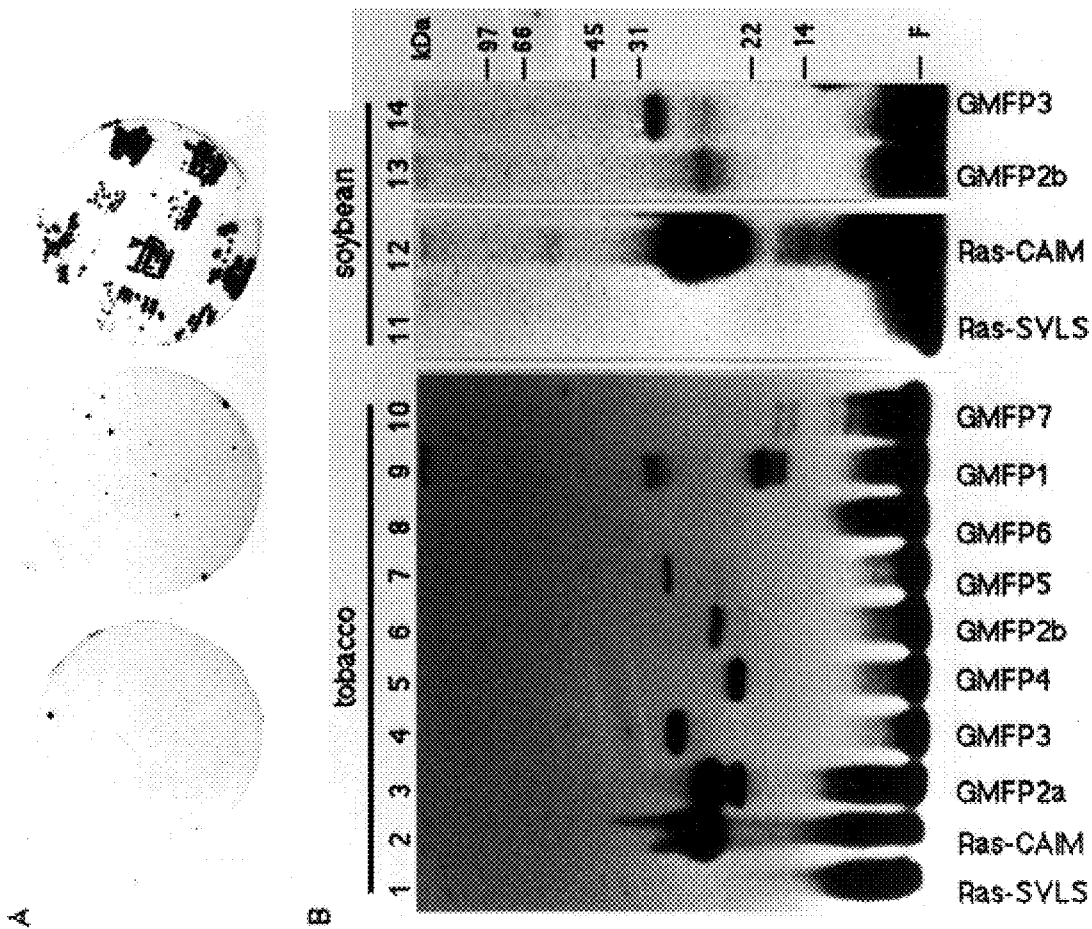
FIG. 2 shows E. coli-expressed soybean proteins which are farnesyl-labeled. (A) [$^3$H] farnesyl labeled colony filter blots. A soybean cDNA library plated at 1×10$^3$ (left) or 3×10$^4$ (center) cells/filter was screened by prenyl labeling colony protein blots as in FIG. 1. Various positive clones were streaked on the filter at right, and the protein blot was prenyl labeled. (B) Protein extracts of E. coli clones selected by library screening were prenylated in vitro and separated by SDS-PAGE. Prenylation was with FTase contained in an extract from tobacco (Lanes 1–10) or soybean (Lanes 11–14). Clones expressing Ras-CAIM or Ras-SVLS are shown as positive and negative controls, respectively. Proteins with the deduced peptide sequences shown in FIG. 3 were as follows: GMFP1 (Glycine max farnesylated protein 1) (lane 9), GMFP2 (identical isolates GMFP2a and b, lanes 3, 6 and 13), GMFP3 (lanes 4, 14), GMFP6, lane 8. Other lanes (5, 7, 10) show proteins expressed from clones which appear to be unique after preliminary sequence analysis, but which have not yet been fully characterized (GMFP4, -5, and -7). The positions and molecular weights of marker proteins are shown at right.

Sequences at the 5' and 3' ends (150–350 bases) of four additional farnesylated protein-encoding cDNAs did not show any similarity to cDNAs described here, or to each other [3]. Three of these prenyl-labeled proteins are shown in FIG. 2B (GMFP4, -5, and -7). Thus, other types of soybean prenylated proteins, whose characterization is in progress, were detected by this procedure.

The carboxy-terminal peptides found on prenylated proteins identified by this screen conform to the consensus CaaX motif recognized by FTases. Furthermore, these peptides are identical or very similar to carboxy-terminal peptides known to be farnesylated in vivo. The carboxy-terminus of GMFP3 (CIIM) is identical to the farnesylated carboxy-terminus of human K-Ras(C-4A) (33, 34). Likewise, the carboxy-terminal tetrapeptide of GMFP1, CAQQ is identical to that of ANJ1 (21). The carboxy-terminal tetrapeptide of GMFP2 (CTIM) is similar to that of chicken prelamin A (CSIM) (16). GMFP6 had the carboxy-terminal CaaX sequence CVIC, identical to that of S. pombe Ras (35). The carboxy-terminus CVVM (identical to that of N-Ras, 36) was encoded 170 bases upstream of the poly (dA) tail of GMFP7 (FIG. 2B).

Our results indicate that this screening method will facilitate the identification of novel prenylated proteins in other systems. GGTase substrates may also be identified by this method. Since the method does not require sensitive detection of proteins ($\geq 0.12$ mmol m$^{-2}$), it is expected that it can be adapted to identify plasmid-encoded proteins with properties other than the covalent linkage of an isoprenoid. Properties conferred by a small linear domain, such as a protein kinase phosphorylation site (37), are expected to be detectable by this method. In addition, other protein characteristics that are retained after protein blotting, such as autophosphorylation (38–40), calcium binding (41), and binding by pharmaceuticals, herbicides or insecticides, may also be detectable on colony blots in accordance with the invention.

Because the hydrophobic prenyl moiety generally promotes membrane association, it is reasonable to expect that many of these farnesylated soybean proteins are membrane localized. The basic repeats found in the deduced GMFP2 and GMFP3 peptides suggest that they could be located in the nucleus and may bind nucleic acids. Our results show that plants contain a diverse array of genes encoding farnesylated proteins, and suggest that fundamental differences in the identities of farnesylated proteins may exist between plants and other eukaryotes.

REFERENCES

The following references are hereby incorporated by reference as if each had been individually incorporated by reference and fully set forth.
1. Moores, S. L, Schaber, M. D., Mosser, S. D., Rands, E., O'Hara, M. B., Garsky, V. M., Marshall, M. S., Pompliano, D. L. and Gibbs, J. B. (1991) *J. Biol. Chem.* 266, 14603–14610.
2. Schafer, W. R., Kim, R., Sterne, R., Thorner, J., Kim, S.-H. and Rine, J. (1989) *Science* 245, 379–384
3. Jackson, J. H., Cochrane, C. G., Bourne, J. R., Solski, P. A., Buss, J. E. and Der, C. J. (1990) *Proc. Natl. Acad. Sci., U.S.A.* 87, 3042–3046
4. Clarke, S. (1992) *Annu. Rev. Biochem.* 61, 355–386
5. Inglese, J., Glickman, J. F., Lorenz, W., Caron, M. G. and Lefkowitz, R. J. (1992) *J. Biol. Chem.* 267, 1422–1425
6. Inglese, J., Koch, W. J., Caron, M. G. and Lefkowitz, R. J. (1992) *Nature* 359, 147–150
7. Maltese, W. A. and Robishaw, J. D. (1990) *J. Biol. Chem.* 265, 18071–18074
8. Fukada, Y., Takao, T., Ohguro, H., Yoshizawa, T., Akino, T. and Shimonishi, Y. (1990) *Nature* 346, 658–660
9. Mumby, S. M., Casey, P. C., Gilman, A. G., Gutowski, S. and Sternweis, P. C. (1990) *Proc. Natl. Acad. Sci. U.S.A.* 87, 5873–5877
10. Wildman, D. E., Tamir, H., Leberer, E., Northup, J. K. and Dennis, M. (1993) *Proc. Natl. Acad. Sci U.S.A.* 90, 794–798
11. Anant, J. S., Ong, O. C., Xie, H., Clarke, S., O'Brien, P. J. and Fung, B. K. -K. (1992) *J. Biol. Chem.* 267, 687–690
12. Bowler, C., Neuhaus, G., Yamagata, H. and Chua, N. -H. (1994) *Cell* 77, 73–81
13. Kearns, E. V. and Assmann, S. M. (1993) *Plant Physiol.* 102, 711–715
14. Kieber, J. J., Rothenberg, M., Roman, G., Feldmann, K. A. and Ecker, J. R. (1993) *Cell* 72, 427–441
15. Wolda, S. L. and Glomset, J. A. (1988) *J. Biol. Chem* 263, 5997–6000
16. Vorburger, K., Kitten, G. T. and Nigg, E. A. (1989) *EMBO J.* 8, 4007–4013
17. Tong, C. -G., Dauwalder, M., Clawson, G. A., Hatem, C. L. and Roux, S. J. (1993) *Plant Physiol.* 101, 1005–1011
18. McNulty, A. K. and Saunders, M. J. (1992) *J. Cell Sci.* 103, 407–414
19. Frederick, S. E., Mangan, M. E., Carey, J. B. and Gruber, P. J. (1992) *Exp. Cell Res.* 199, 213–222
20. Randall, S. K., Marshall, M. S. and Crowell, D. N. (1993) *Plant Cell* 5, 433–442
21. Zhu, J. -K., Bressan, R. A. and Hasegawa, P. M. (1993) *Proc. Natl. Acad. Sci., U.S.A.* 90, 8557–8561
22. Zhu, J. -K., Shi, J., Bressan, R. A. and Hasegawa, P. M. (1993) *Plant Cell* 5, 341–349
23. Yang, Z. and Watson. J. C. (1993) *Proc. Natl. Acad. Sci. U.S.A.* 90, 8732–8736
24. Bednarek, S. Y., Reynolds, T. L., Schroeder, M., Grabowski, R., Hengst, L., Gallwitz, D. and Raikhel, N. V. (1994) *Plant Physiol.* 104, 591–596
25. Terryn, N., Van Montagu, M. and Inzé, D. (1993) *Plant Mol. Biol.* 22, 143–152
26. James, G. L., Goldstein, J. L., Pathak, R. K., Anderson, R. G. W., and Brown, M. S. (1994) *J. Biol. Chem.* 269, 14182–14190
27. Stein, R. B., Robinson, P. S. and Scolnick, E. M. (1984) *J. Virol.* 50, 343–351
28. Temeles, G. L., Gibbs, J. B., D'Alonzo, J. S., Sigal, I. S. and Scolnick, E. M. (1985) *Nature* 313, 700–703
29. Sambrook, J., Fritsch, E. F. and Maniatis, T. (1989) *Molecular cloning: a Laboratory Manual.* (Cold Spring Harbor Laboratory, Cold Spring Harbor, N.Y.)
30. Crowell, D. N. and Amasino, R. M. (1991) *Plant Physiol.* 95, 711–715
31. Kinsella, B. T. and Maltese, W. A. (1992) *J. Biol. Chem.* 267, 3940–3945
32. Pearson, W. R. and Lipman, D. J. (1988) *Proc. Natl. Acad. Sci., U.S.A.,* 85, 2444–244
33. Shimizu, K., Birnbaum, D., Ruley, M. A., Fasano, O., Suard, Y., Edlund, L., Taparowsky, E., Goldfarb, M. and Wigler, M. (1983) *Nature* 304, 497–500

34. McGrath, J. P., Capon, D. J., Smith, D. H., Chen, E. Y., Seeburg, P. H., Goeddel, D. V. and Levinson, A. D. (1983) *Nature* 304, 501–506

35. Fukui, Y. and Kaziro, Y. (1985) *EMBO J.* 4, 687–694

36. Hancock, J. F., Magee, A. I., Childs, J. E. and Marshall, C. J. (1989) *Cell* 57, 1167–1177

37. Kennelly P. J. and Krebs, E. G. (1991) *J. Biol. Chem.* 266, 15555–15558

38. Celenza J. L. and Carlson, M. (1986) *Science* 233, 1175–1180

39. Battey, N. H. and Venis, M. A. (1988) *Planta* 176, 91–97

40. Maru, L. Y. and Witte, O. N. (1991) *Cell* 67, 459–468

41. Davis, T. N., Urdea, M. S., Masiarz, F. R. and Thorner, J. (1986) *Cell* 47, 423

---

What is claimed is:

1. A method for identifying a transformant containing DNA encoding a protein capable of being prenylated, comprising:

establishing a pattern of distinct colonies of Escherichia or Salmonella bacteria from a cDNA expression library on a first substrate, the expression library containing introduced cDNA;

replicating said pattern of distinct colonies on a least a second substrate;

causing protein synthesis by said distinct colonies on said second substrate and creating a protein blot therefrom containing distinct areas of protein corresponding to the distinct colonies;

subjecting the protein blot to prenylation conditions with a labeled prenylation agent to label one or more protein areas which contain prenylated protein;

detecting said one or more protein areas which have been labeled by said labeled prenylation agent; and correlating said one or more protein areas containing a prenylated protein to said first substrate to identify one or more transformant bacteria containing cDNA encoding a protein capable of being prenylated.

2. A method for identifying a transformant containing a eukaryotic cDNA encoding a subject protein, the subject protein being capable of being prenylated, the method comprising:

establishing a pattern of distinct colonies of Escherichia or Salmonella bacteria from a eukaryotic cDNA expression library on a first substrate, the eukaryotic cDNA expression library containing introduced eukaryotic cDNA;

replicating said pattern of distinct colonies on at least a second substrate;

causing protein synthesis by said distinct colonies on said second substrate and creating a protein blot therefrom containing distinct areas of protein corresponding to the distinct colonies;

subjecting the protein blot to prenylation conditions with a labeled prenylation agent in order to label one or more protein areas which contain the subject protein;

detecting said one or more protein areas which have been labeled; and correlating said one or more protein areas containing the subject protein to said first substrate to identify one or more transformant bacteria containing eurkaryotic cDNA encoding the subject protein.

3. A method for obtaining and using a labeled protein blot useful in the identification of a transformant containing eukaryotic cDNA encoding a subject protein, the subject protein being capable of being prenylated, the method comprising:

providing a protein blot comprising a replicate substrate having expressed protein from a pattern of distinct colonies of Escherichia or Salmonella bacteria from a eukaryotic cDNA expression library containing introduced eukaryotic cDNA, said pattern of distinct colonies being a replica of a pattern of distinct colonies on an original substrate; and subjecting the protein blot to prenylation conditions with a labeled prenylation agent in order to identify one or more protein areas which contain the subject protein; and said one or more protein areas being correlatable to said original substrate to identify a colony containing transformants expressing the subject protein.

4. The method of claim 1, wherein said bacteria are Escherichia bacteria.

5. The method of claim 2 wherein said bacteria are Escherichia bacteria.

6. The method of claim 3, wherein said bacteria are Escherichia bacteria.

7. The method of claim 4, wherein said bacteria are *Escherichia coli.*

8. The method of claim 5, wherein said bacteria are *Escherichia coli.*

9. The method of claim 6, wherein said bacteria are *Escherichia coil.*

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH:   86 amino acids
      (B) TYPE:     amino acid
      (D) TOPOLOGY: linear (ii) MOLECULE TYPE: protein (xi) SEQUENCE DESCRIPTION:   SEQ ID NO:1:

```
Leu Tyr Ile Gln Phe Asn Val Asp Phe Pro Asp Ser Gly Phe Leu
                 5                  10                  15

Ser Pro Asp Gln Cys Gln Leu Leu Glu Lys Val Leu Pro Gln Lys
                20                  25                  30

Ser Ser Lys His Val Ser Asp Met Glu Leu Asp Asp Cys Glu Glu
                35                  40                  45

Thr Thr Leu His Asp Val Asn Phe Lys Glu Glu Met Arg Arg Lys
                50                  55                  60

Gln Gln Gln Gln Tyr Arg Glu Ala Tyr Asp Glu Asp Asp Asp Glu
                65                  70                  75

Pro Ser Gly Gln Arg Val Gln Cys Ala Gln Gln
                80                  85
```

(2) INFORMATION FOR SEQ ID NO:2:

(i) SEQUENCE CHARACTERISTICS:
      (A) LENGTH:   84 amino acids
      (B) TYPE:     amino acid
      (D) TOPOLOGY: linear (ii) MOLECULE TYPE:   protein (xi) SEQUENCE DESCRIPTION: SEQ ID NO:2:

```
Met Tyr Ile His Phe Thr Val Glu Phe Pro Asp Ser Leu Asn Pro
 1               5                  10                  15

Asp Gln Val Lys Ser Leu Glu Ala Ile Leu Pro Pro Lys Pro Ser
                20                  25                  30

Met Ser Leu Thr Tyr Met Glu Leu Asp Glu Cys Glu Glu Thr Thr
                35                  40                  45

Leu His Asn Val Asn Ile Glu Glu Glu Met Lys Arg Lys Gln Thr
                50                  55                  60

Gln Ala Gln Gln Glu Ala Tyr Asp Glu Asp Asp Glu Pro Ala Gly
                65                  70                  75

Gly Gln Arg Val Gln Cys Ala Gln Gln
                80
```

(2) INFORMATION FOR SEQ ID NO:3:

(i) SEQUENCE CHARACTERISTICS:
        (A) LENGTH:    130 amino acids
        (B) TYPE:      amino acid
        (D) TOPOLOGY:  linear (ii) MOLECULE TYPE: protein (xi) SEQUENCE DESCRIPTION:SEQ ID NO:3:

Lys Ala Glu Lys Pro Lys Thr Glu Pro Glu Lys Lys Lys Asp Gly
              5                  10                  15

Gly Gly Glu Lys Pro Lys Glu Glu Pro Glu Lys Lys Lys Asp Gly
             20                  25                  30

Gly Glu Lys Pro Lys Pro Gly Pro Glu Lys Pro Lys Asp Lys Pro
             35                  40                  45

Thr Pro Ala Pro Leu Pro Val Gln Pro His Ile Ala Ala Pro Met
             50                  55                  60

Ala Val Pro Val Gly Met Leu Tyr Ala Pro Pro Cys Tyr Gly
             65                  70                  75

Gly Arg Pro Val Gly Pro Gly Tyr Glu Tyr Gly Gly Pro Met Leu
             80                  85                  90

Cys Tyr Asp Gly Tyr Tyr Ala Arg Pro Val Tyr Asp Ser Tyr Ser
             95                 100                 105

Gly Gly Arg Pro Cys Tyr Gly Asn Arg Cys Asp Gln Tyr Phe Ser
            110                 115                 120

Glu Glu Asn Pro Gln Gly Cys Thr Ile Met
            125                 130

(2) INFORMATION FOR SEQ ID NO:4:

(i) SEQUENCE CHARACTERISTICS:
        (A) LENGTH:    154 amino acids
        (B) TYPE:      amino acid
        (D) TOPOLOGY:  linear (ii) MOLECULE TYPE: protein (xi) SEQUENCE DESCRIPTION:    SEQ ID NO:4:

Lys Pro Lys Ala Glu Pro Glu Lys Lys Lys Asp Gly Gly Gly Glu
              5                  10                  15

Lys Pro Lys Ala Glu Pro Glu Lys Lys Lys Asp Gly Gly Gly Glu
             20                  25                  30

Lys Pro Lys Ala Glu Pro Glu Lys Lys Lys Asp Gly Gly Glu Lys
             35                  40                  45

Pro Lys Gly Asp Ala Pro Lys Lys Glu Ala Glu Lys Pro Lys Pro
             50                  55                  60

Gly Pro Glu Lys Pro Lys Asp Lys Pro Ala Pro Ala Pro Leu Pro
             65                  70                  75

Val Gln Pro His Met Ala Ala Pro Met Ala Val Pro Val Gly Met
             80                  85                  90

Leu Tyr Ala Pro Pro Cys Tyr Glu Gly Arg Pro Val Gly Pro
             95                 100                 105

Gly Tyr Glu Tyr Gly Gly Pro Met Phe Cys Tyr Asp Gly Tyr Tyr
            110                 115                 120

Ala Arg Pro Val Tyr Asp Ser Tyr Gly Gly Arg Pro Cys Tyr
            125                 130                 135

Val Asn Arg Gly Asp Gln Tyr Phe Ser Glu Glu Asn Pro Gln Gly
            140                 145                 150

Cys Ile Ile Met (2) INFORMATION FOR SEQ ID NO:5:

(i) SEQUENCE CHARACTERISTICS:
        (A) LENGTH:   74 amino acids
        (B) TYPE:     amino acid
        (D) TOPOLOGY: linear (ii) MOLECULE TYPE: protein (xi) SEQUENCE DESCRIPTION:   SEQ ID NO:5:

```
Lys Leu Arg Lys Phe Cys His Val Glu Ile Leu Ser Val Gly Pro
                 5                  10                  15

Ala Lys Glu Glu Pro Lys Lys Glu Glu Lys Lys Pro Glu Ala Lys
                20                  25                  30

Lys Asp Pro Lys Glu Glu Tyr Ala Glu Leu Leu Lys Val Val Glu
                35                  40                  45

Ala Asn Tyr Tyr Gln Thr Arg His Leu Gln Tyr Pro Tyr Tyr Tyr
                50                  55                  60

Ser Arg Thr Val Glu Glu Asn Pro Thr Gly Cys Val Ile Cys
                65                  70
```